US012751702B2

(12) United States Patent
Kawayoke et al.

(10) Patent No.: US 12,751,702 B2
(45) Date of Patent: Oct. 6, 2026

(54) BIOPSY DEVICE AND SPECIMEN COLLECTION METHOD

(71) Applicant: OLYMPUS CORPORATION, Tokyo (JP)

(72) Inventors: Shoichiro Kawayoke, Tokyo (JP); Shohei Kamada, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 361 days.

(21) Appl. No.: 18/383,932

(22) Filed: Oct. 26, 2023

(65) Prior Publication Data

US 2024/0050077 A1 Feb. 15, 2024

Related U.S. Application Data

(63) Continuation of application No. PCT/JP2022/020325, filed on May 16, 2022.

(Continued)

(51) Int. Cl.
*A61B 10/04* (2006.01)
*A61B 10/02* (2006.01)

(52) U.S. Cl.
CPC .......... *A61B 10/04* (2013.01); *A61B 10/0266* (2013.01); *A61B 2010/045* (2013.01)

(58) Field of Classification Search
CPC ................ A61B 10/04; A61B 10/0266; A61B 2010/045; A61B 2010/0208
See application file for complete search history.

(56) References Cited

U.S. PATENT DOCUMENTS

2003/0114773 A1* 6/2003 Janssens ............ A61B 10/0233 600/564
2004/0064136 A1* 4/2004 Papineau ........... A61B 17/3421 606/41

(Continued)

FOREIGN PATENT DOCUMENTS

EP 2946732 A1 11/2015
EP 2982309 A1 2/2016

(Continued)

OTHER PUBLICATIONS

International Search Report and Written Opinion dated Jul. 19, 2022 issued in PCT/JP2022/020325, with partial translation.

(Continued)

*Primary Examiner* — Jason M Sims
*Assistant Examiner* — Kyle W. Kretzer
(74) *Attorney, Agent, or Firm* — Scully, Scott, Murphy & Presser, P.C.

(57) ABSTRACT

A biopsy device includes: a hollow needle; a wire located inside the needle and having a helical drill portion; a rotation mechanism moving the drill portion; a sheath covering the needle, the needle and the wire being movable in a longitudinal direction of the needle with respect to the sheath; and an operating unit on a proximal side of the needle, the wire, and the sheath. The unit includes: a main body fixed to a proximal end of the sheath; and a knob fixed to a proximal end of the wire and supported by the main body so as to be movable in the longitudinal direction and rotatable about a longitudinal axis of the wire. The mechanism includes: a threaded portion, on the main body, having a pitch equal to a pitch of the drill portion; and a joint portion, on the knob, joined to the threaded portion.

14 Claims, 17 Drawing Sheets

Related U.S. Application Data

(60) Provisional application No. 63/189,793, filed on May 18, 2021.

(56) References Cited

U.S. PATENT DOCUMENTS

| | | | | |
|---|---|---|---|---|
| 2007/0027464 | A1 | 2/2007 | Way et al. | |
| 2007/0055215 | A1 | 3/2007 | Tran et al. | |
| 2012/0289901 | A1* | 11/2012 | Fink ................... | A61B 17/3478 604/117 |
| 2014/0005671 | A1 | 1/2014 | Solsberg et al. | |
| 2014/0024933 | A1 | 1/2014 | Solsberg et al. | |
| 2014/0026693 | A1 | 1/2014 | Eller | |
| 2015/0313580 | A1 | 11/2015 | Dejima et al. | |
| 2016/0030014 | A1 | 2/2016 | McWeeney et al. | |
| 2016/0030015 | A1 | 2/2016 | McWeeney et al. | |
| 2016/0030016 | A1 | 2/2016 | McWeeney et al. | |
| 2016/0030017 | A1 | 2/2016 | McWeeney et al. | |
| 2016/0030018 | A1 | 2/2016 | McWeeney et al. | |
| 2016/0074021 | A1 | 3/2016 | Dejima et al. | |
| 2016/0324536 | A1 | 11/2016 | Takahashi | |

FOREIGN PATENT DOCUMENTS

| | | | |
|---|---|---|---|
| EP | 2997902 | A2 | 3/2016 |
| EP | 3005949 | A1 | 4/2016 |
| EP | 3184055 | A1 | 6/2017 |
| JP | H0319847 | A | 4/1991 |
| JP | 2011024789 | A | 2/2011 |
| JP | 2012235878 | A * | 12/2012 |
| JP | 5997297 | B2 | 9/2016 |
| JP | 6078117 | B2 | 2/2017 |
| JP | 6078118 | B2 | 2/2017 |
| JP | 6097826 | B2 | 3/2017 |
| JP | 6430697 | B2 | 11/2018 |
| WO | 2007016683 | A2 | 2/2007 |
| WO | 2007016686 | A2 | 2/2007 |
| WO | 2014192646 | A1 | 12/2014 |
| WO | 2016027523 | A1 | 2/2016 |

OTHER PUBLICATIONS

International Search Report and Written Opinion dated Jun. 28, 2022 issued in PCT/JP2022/020318, with partial translation.

* cited by examiner

BIOPSY DEVICE AND SPECIMEN COLLECTION METHOD

CROSS-REFERENCE TO RELATED APPLICATIONS

This application is based upon and claims the benefit of priority from U.S. Provisional Application No. 63/189,793, filed on May 18, 2021; the entire contents of which are incorporated herein by reference.

This is a continuation of International Application PCT/JP2022/020325 which is hereby incorporated by reference herein in its entirety.

TECHNICAL FIELD

The present invention relates to a biopsy device and a specimen collection method.

BACKGROUND ART

Conventional biopsy methods such as endoscopic ultrasound-guided fine needle aspiration (EUS-FNA) or endoscopic ultrasound-guided fine needle biopsy (EUS-FNB), in which a hollow needle is inserted into living tissue under ultrasound observation and a portion of the living tissue is collected as a specimen, are known (see, for example, PTL 1 and PTL 2). One of the challenges of such biopsy methods is an amount of specimen collected. Because the needle inserted into the body via the endoscope's instrument channel is small in diameter, it is difficult to collect a sufficient amount of specimen for diagnosis. In PTL 1 and PTL 2, a distal end of the needle is formed in a helical shape to improve the amount of specimen collected.

CITATION LIST

Patent Literature

{PTL 1}

The Publication of Japanese Patent No. 6430697

{PTL 2}

Japanese Unexamined Patent Application, Publication No. 2012-235878

SUMMARY OF INVENTION

One aspect of the present invention is a biopsy device including: a hollow needle; a wire located inside the needle in a longitudinal direction of the needle and having a helical drill portion at a distal end portion; a rotation mechanism configured to move the drill portion in the longitudinal direction, the drill portion protruding from a distal end of the needle and rotating about a longitudinal axis of the wire; a long-length sheath covering the needle, the needle and the wire being movable in the longitudinal direction with respect to the sheath; and an operating unit provided on a proximal side of the needle, the wire, and the sheath, wherein the operating unit includes: a main body fixed to a proximal end of the sheath; and a knob fixed to a proximal end of the wire and supported by the main body so as to be movable in the longitudinal direction and rotatable about the longitudinal axis, and the rotation mechanism includes: a threaded portion provided on the main body and having a pitch equal to a pitch of the drill portion; and a joint portion provided on the knob and being joined to the threaded portion.

DESCRIPTION OF EMBODIMENTS

First Embodiment

A biopsy device and a specimen collection method according to a first embodiment of the invention will be described with reference to the accompanying drawings.

Figure 1A:
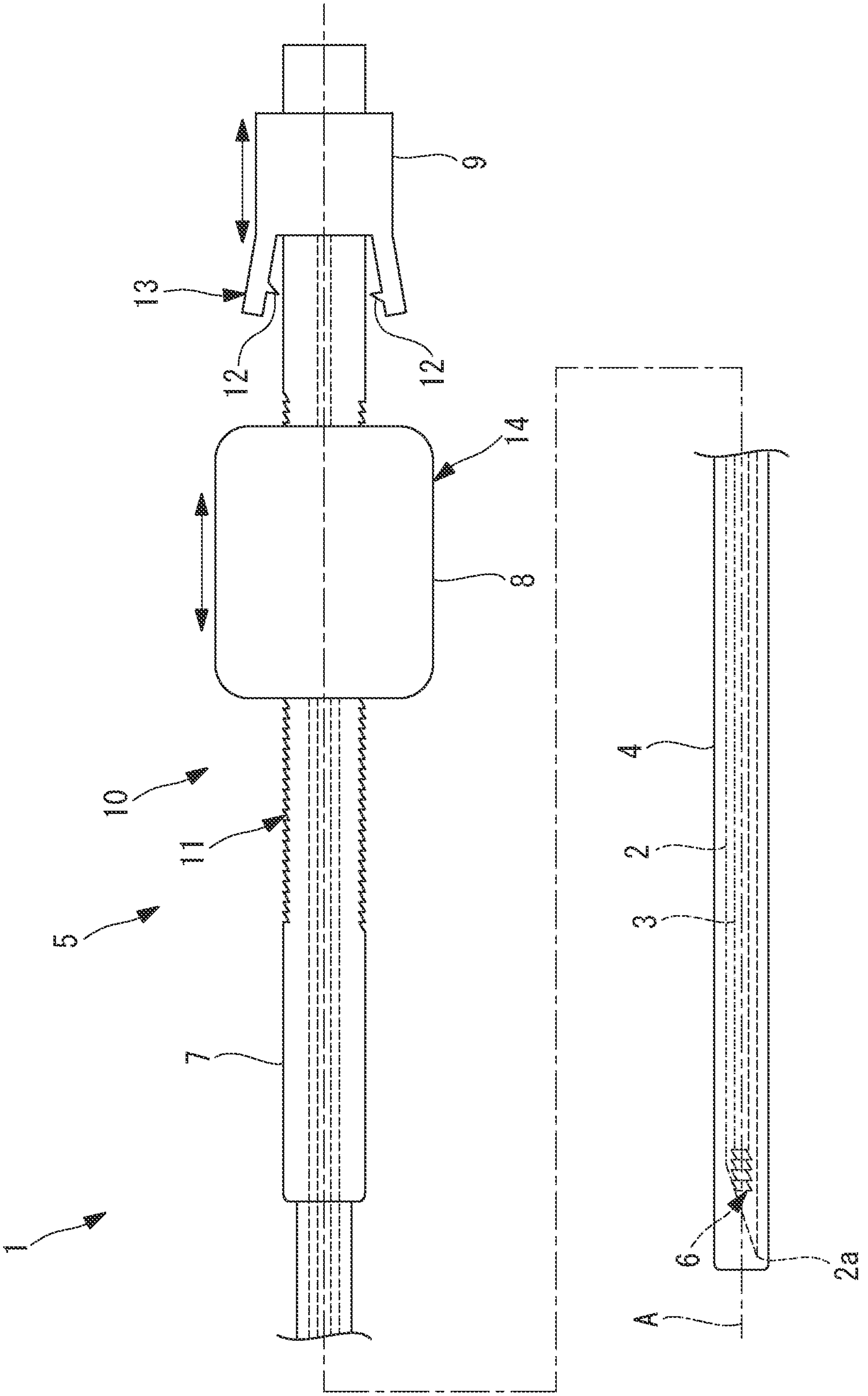
FIG. 1A is a diagram showing an overall configuration of a biopsy device according to a first embodiment, with a threaded portion released from a joint portion.
Figure 1B:
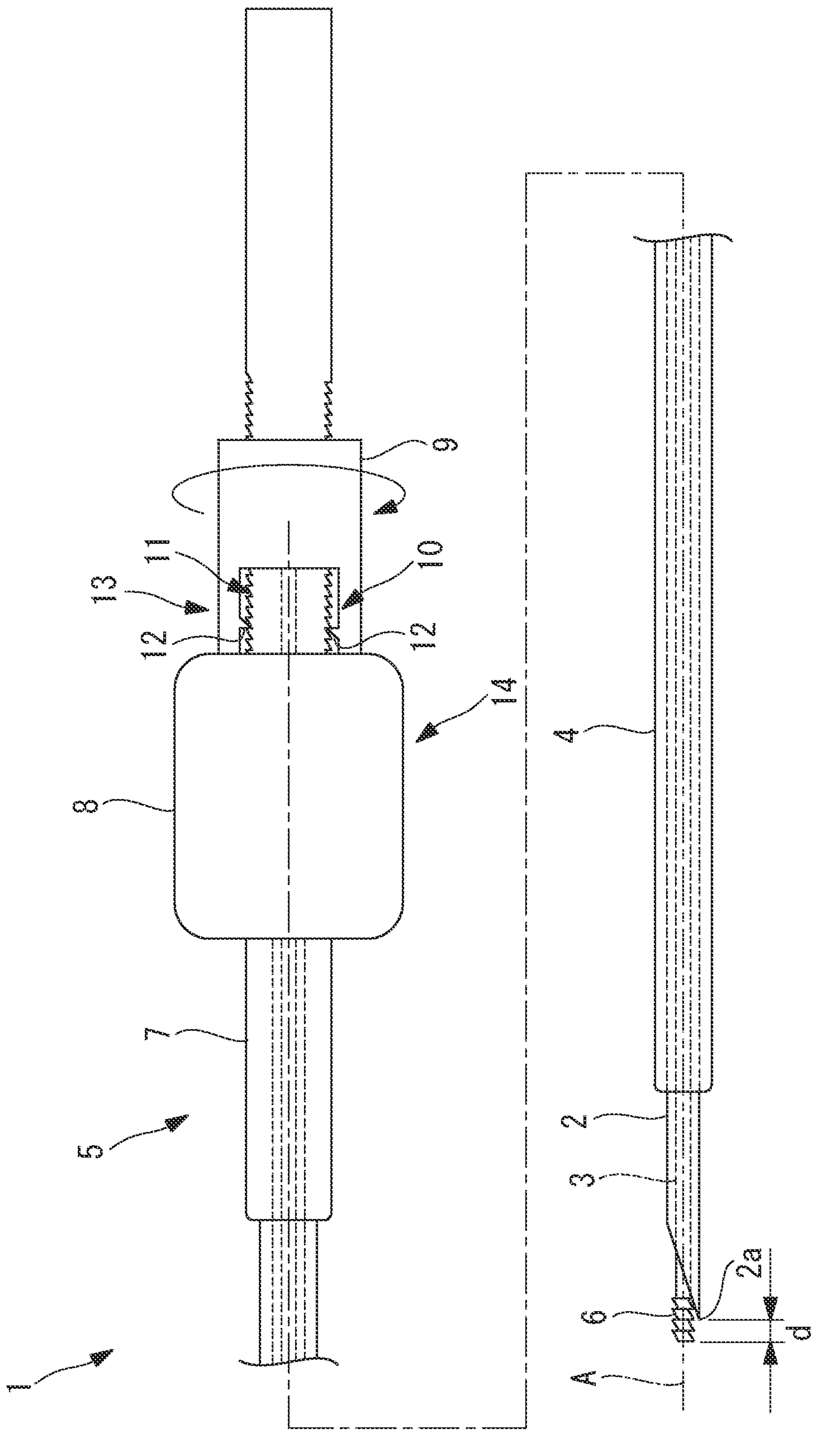
FIG. 1B is a diagram showing the biopsy device shown in FIG. 2A with a wire positioned by a positioning mechanism and the joint portion joined to the threaded portion.

As shown in FIGS. 1A and 1B, the biopsy device 1 according to this embodiment has a hollow needle 2, a wire 3 located in the needle 2, a long-length sheath 4 covering the needle 2, and an operating unit 5 provided on a proximal side of the needle 2, the wire 3, and the sheath 4.

The biopsy device 1 is used in combination with an ultrasound endoscope. The needle 2, the wire 3, and, the sheath 4 are inserted into a treatment instrument channel of the ultrasound endoscope, and the operating unit 5 is located outside the ultrasound endoscope. Distal ends of the needle 2, the wire 3, and the sheath 4 protruding from a distal end of the ultrasound endoscope are located within a field of view of the ultrasound endoscope and are observed in an optical image and an ultrasound image acquired with the ultrasound endoscope.

The needle 2 and the sheath 4 are tubular members that are flexible and open at both ends. The needle 2 has a sharp needle tip 2*a* at its distal end. The needle 2 is located in a longitudinal direction of the sheath 4 inside the sheath 4, and the flexible wire 3 is located in the longitudinal direction of the needle 2 inside the needle 2. The needle 2, the wire 3, and the sheath 4 are movable in the longitudinal direction with respect to each other, and the wire 3 is rotatable about a longitudinal axis A of the wire 3 with respect to the needle 2 and the sheath 4.

Figure 2:
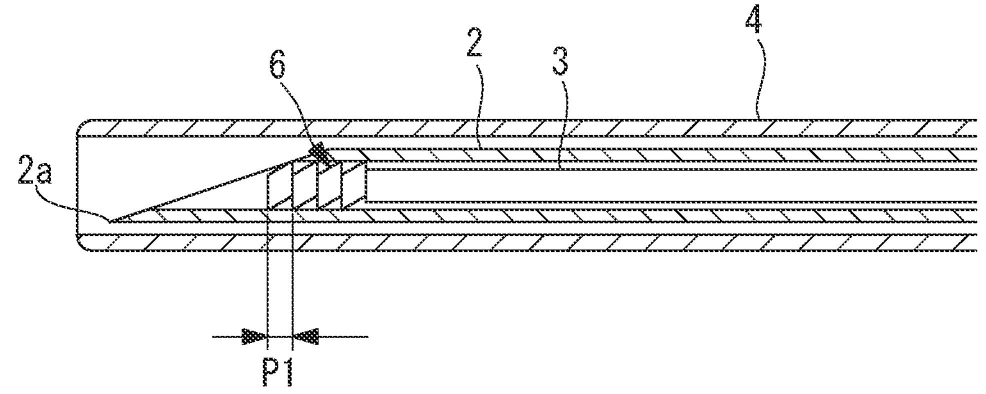
FIG. 2 is an enlarged view of a distal portion of the biopsy device in FIG. 1A, illustrating a drill portion

As shown in FIG. 2, the wire 3 has a helical drill portion 6 at a distal end portion. The drill portion 6 has a helical groove that coils helically about the longitudinal axis A and has a predetermined pitch P1 in the longitudinal direction. A distal end of the drill portion 6 may be a sharply pointed portion so that it can be easily inserted into living tissue. The drill portion 6 is formed, for example, by machining a helical groove on an outer circumference of the cylindrical distal end portion of the wire 3. Such a solid drill portion 6 has high rigidity, so that the drill portion 6 is not easily deformed when it is inserted into and withdrawn from the living tissue.

As described below, the drill portion 6 is rotated when the wire 3 is rotated by operating a knob 9 of the operating unit 5. For efficiently transmitting the rotation from a proximal end of the wire 3 to the drill portion 6, an outer diameter of the wire 3 should preferably be thick. On the other hand, for ensuring a space for capturing living tissue inside the needle 2, the wire 3 should preferably be thin. The outer diameter of the wire 3 is appropriately designed based on both the transmission efficiency of rotation and the volume of the space inside the needle 2.

The operating unit 5 has a main body 7 fixed to a proximal end of the sheath 4, a slider 8 fixed to a proximal end of the needle 2, and the knob 9 fixed to the proximal end of the wire 3.

The main body 7 is an approximately cylindrical member that extends coaxially with the sheath 4.

The slider 8 and the knob 9 are annular or tubular members that are located on a radially outer side of the main body 7 and are supported by the main body 7 so that it is movable in the longitudinal direction. The knob 9 is supported by the main body 7 so that it is rotatable about a central axis of the main body 7 that coincides with the longitudinal axis A.

As shown in FIG. 1A, when the slider 8 and the knob 9 are located in the initial position, the needle tip 2*a* and the drill portion 6 are stored within the sheath 4. As shown in FIG. 1B, an operator can push the slider 8 and the knob 9 toward the distal side to advance the needle 2 and the wire 3 toward the distal side, thereby causing the needle tip 2*a* and the drill portion 6 to protrude from the distal end of the sheath 4. The operator can also retract the needle 2 and the wire 3 to the proximal side by pulling the slider 8 and the knob 9 to the proximal side.

Figure 3:
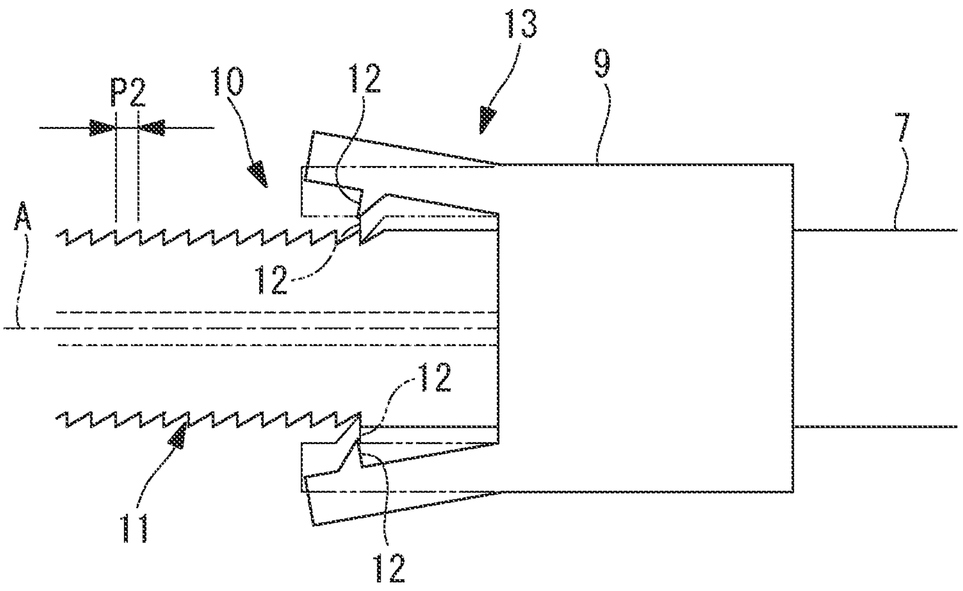
FIG. 3 is an enlarged view of an operating unit of the biopsy device shown in FIG. 1A, illustrating a rotation mechanism.

As shown in FIG. 3, the biopsy device 1 further includes a rotation mechanism 10 that moves the drill portion 6, which rotates about the longitudinal axis A, in the longitudinal direction, a release mechanism 13 that releases a joint between a threaded portion 11 and a joint portion 12 of the rotation mechanism 10, and a positioning mechanism 14 that positions the wire 3 with respect to the needle 2.

The rotation mechanism 10 converts rotation about the longitudinal axis A into movement in a direction along the longitudinal axis A. To be specific, the rotation mechanism 10 has the threaded portion 11 provided on the main body (peripheral member) 7 and the joint portion 12 provided on the knob (wire-side member) 9 and configured to be joined to the threaded portion 11.

The threaded portion 11 has a threaded groove formed on an outer circumference of the main body 7. The joint portion 12 is a projection provided on an inner circumference of the knob 9 and projecting in a radially inward direction and may be a thread having a pitch equal to the threaded groove of the threaded portion 11.

The threaded portion 11 has a pitch P2 equal to the predetermined pitch P1 of the drill portion 6. Hence, rotating the knob 9 with the joint portion 12 joined to the threaded groove of the threaded portion 11 causes the wire 3 to move in the longitudinal direction with a lead equal to the predetermined pitch P1. The lead is an amount of movement in the longitudinal direction per rotation.

In FIG. 3, the joint portion 12 indicated by a solid line shows a state where a joint to the threaded portion 11 is released, and the joint portion 12 indicated by a double-dotted line shows a state where it is joined to the threaded portion 11. The release mechanism 13 consists of an end portion of the knob 9 which is provided with the joint portion 12 and can be displaced. Displacement of the end portion of the knob 9 causes the joint portion 12 to move between a position where it is joined to the threaded portion 11 and a position where the joint to the threaded portion 11 is released. The displacement of the end portion of the knob 9 is brought, for example, by partial deformation of the knob 9.

As shown in FIG. 1A, in the state where the joint between the joint portion 12 and the threaded portion 11 is released, the knob 9 and the wire 3 are translatable in the longitudinal direction with respect to the main body 7 and the sheath 4. As shown in FIG. 1B, with the joint portion 12 joined to the threaded portion 11, the knob 9 and the wire 3 can move in the longitudinal direction with the lead equal to the predetermined pitch P1 while rotating, as described above.

The positioning mechanism 14 consists of the slider 8 that is located distal to the knob 9 and against which the knob 9 butts. In other words, as shown in FIG. 1B, when the knob 9 butts against the slider 8, the wire 3 is positioned, with respect to the needle 2, in a position where the distal end of the drill portion 6 protrudes a predetermined distance d from the needle tip 2*a*. In this state, rotation of the knob 9 causes the needle 2 to move toward the distal side in conjunction with the movement of the wire 3 toward the distal side. The predetermined distance d is a distance at which the drill portion 6 partially protrudes, for example, several millimeters from the needle tip 2*a*.

The configuration of the positioning mechanism 14 described above is an example, and any configuration of the positioning mechanism that can position the wire 3 at a position where the distal end of the drill portion 6 protrudes the predetermined distance d from the needle tip 2*a* may be employed.

The following will explain the specimen collection method according to this embodiment using the biopsy device 1.

Figure 4:
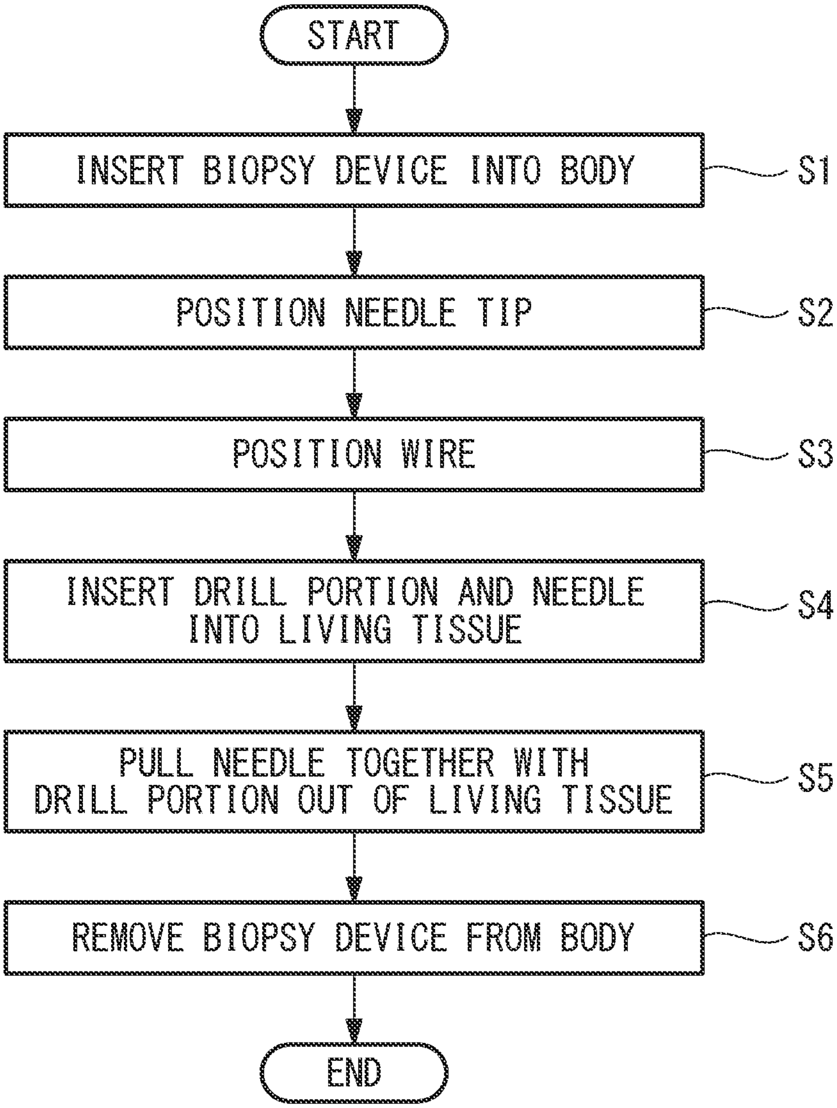
FIG. 4 is a flowchart of a specimen collection method according to the first embodiment.

As shown in FIG. 4, the specimen collection method includes step S1 of inserting the biopsy device 1 into the body, step S2 of positioning the needle tip 2*a* with respect to the target living tissue T, step S3 of positioning the drill portion 6 with respect to the needle 2 via the wire 3, step S4 of inserting the drill portion 6 and the needle 2 into the living tissue T, step S5 of pulling the needle 2 together with the drill portion 6 out of the living tissue T, and step S6 of removing the biopsy device 1 from the body.

Prior to step S1, the ultrasound endoscope is inserted into the body cavity and is located in a position where the target living tissue T is observed. The target living tissue T is, for example, diseased tissue such as cancer formed in a pancreas, and the ultrasound endoscope is inserted through a mouth into a stomach or a duodenum.

Figure 5A:
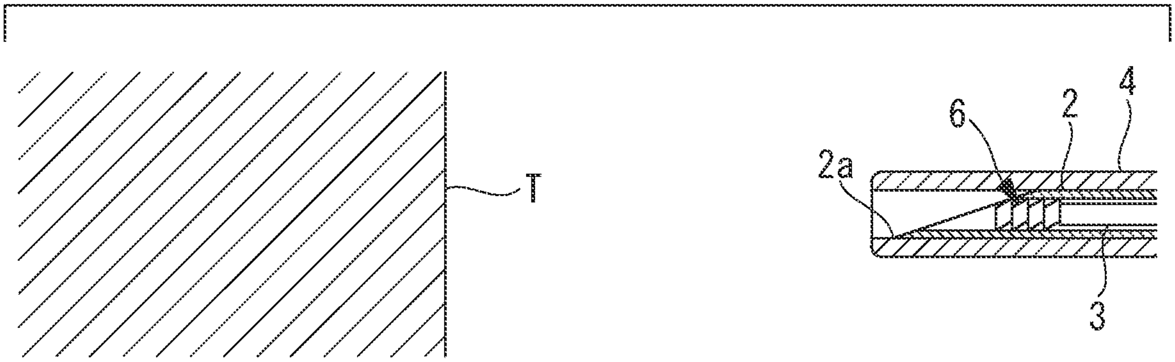
FIG. 5A is a diagram for explaining an operation of the biopsy device in step S1 of the specimen collection method.

In step S1, the operator locates the slider 8 and the knob 9 in their initial positions, confirms that the needle tip 2*a* and the drill portion 6 are accommodated in the sheath 4, and inserts the sheath 4 into the treatment channel of the ultrasound endoscope. As shown in FIG. 5A, the operator locates the distal end of the sheath 4 in an appropriate position with respect to the target living tissue T while observing the optical or the ultrasound image on the ultrasound endoscope.

Figure 5B:
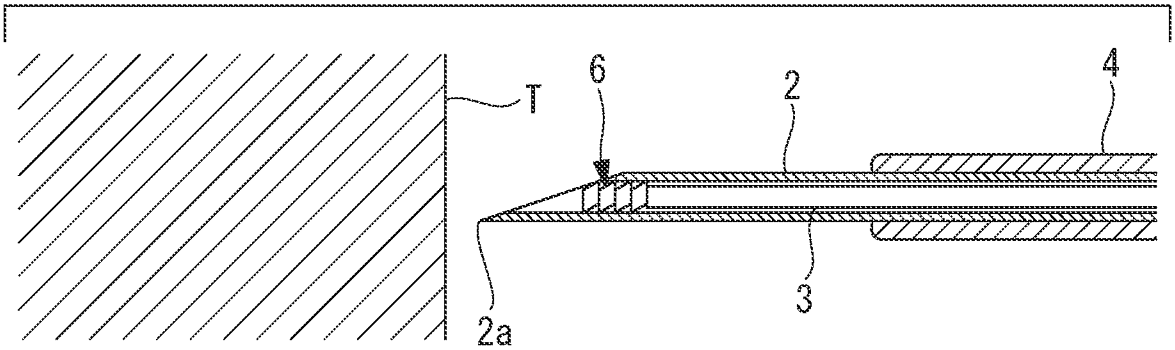
FIG. 5B is a diagram for explaining an operation of the biopsy device in step S2 of the specimen collection method.

Next, in step S2, in the state where the joint between the joint portion 12 and the threaded portion 11 is released, the operator simultaneously pushes the slider 8 and the knob 9 to advance the needle 2 and the wire 3 simultaneously while observing the ultrasound image, thereby positioning the needle tip 2*a* near the target living tissue T (FIG. 5B).

Figure 5C:
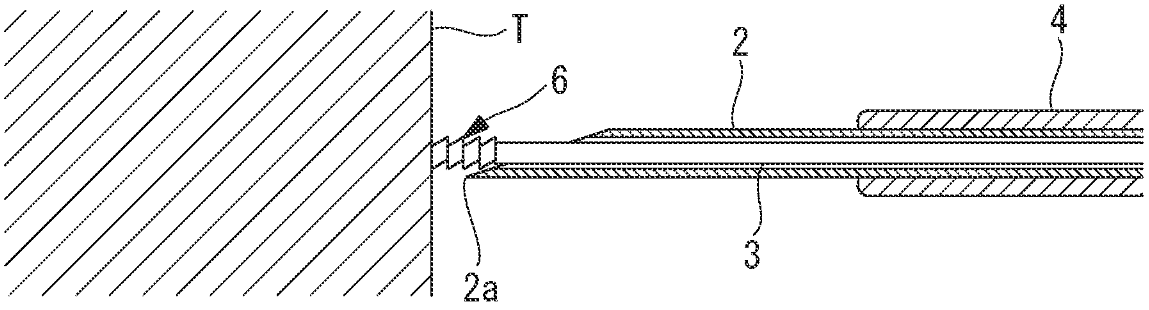
FIG. 5C is a diagram for explaining an operation of the biopsy device in step S3 of the specimen collection method.

Next, in step S3, the operator pushes the knob 9 until it butts against the slider 8, and positions the drill portion 6 through the wire 3 to a position where it protrudes the predetermined distance d from the needle tip 2*a* (FIG. 5C).

Figure 5D:
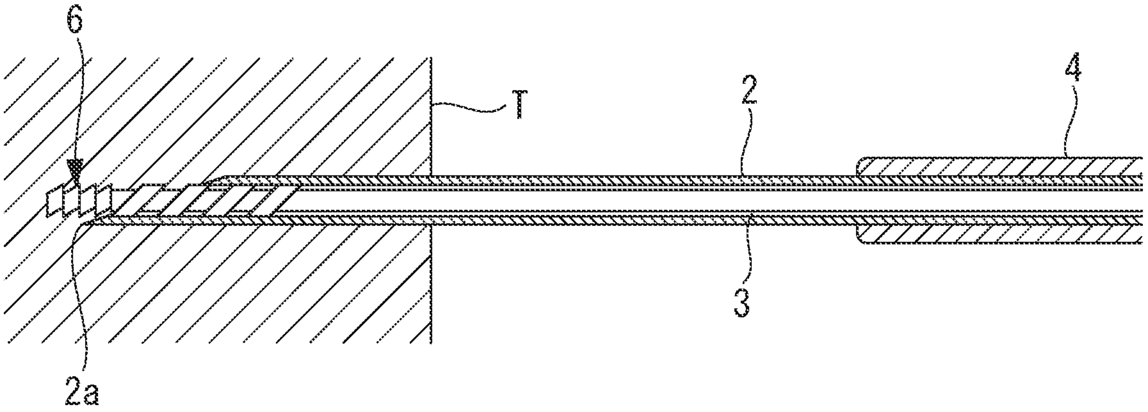
FIG. 5D is a diagram for explaining an operation of the biopsy device in step S4 of the specimen collection method.

Next, in step S4, the operator joins the joint portion 12 to the threaded portion 11, and then, by rotating the knob 9, advances the needle 2 in the longitudinal direction while advancing the drill portion 6 in the longitudinal direction, thereby simultaneously inserting the drill portion 6 and the needle 2 to a desired depth (a predetermined distance) in the living tissue T (FIG. 5D).

At this time, the rotation mechanism 10 consisting of the threaded portion 11 and the joint portion 12 causes the drill portion 6 to advance in the longitudinal direction with the lead equal to the predetermined pitch P1 while rotating about the longitudinal axis A. As a result, the drill portion 6 advances while taking the living tissue T into the helical groove and cutting it into a helical shape. The cut-out, one continuous string of living tissue T is ejected toward the proximal end along the helical groove and captured into the needle 2.

Figure 5E:
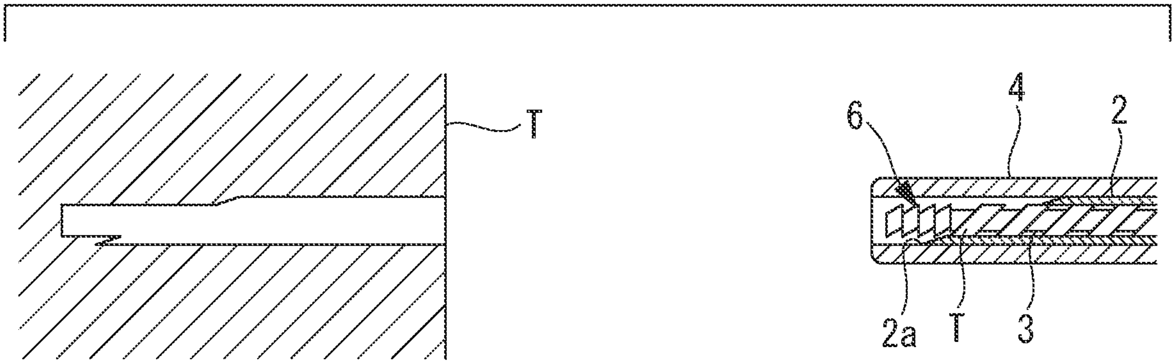
FIG. 5E is a diagram for explaining an operation of the biopsy device in step S5 of the specimen collection method.

Next, in step S5, the operator releases the joint between the threaded portion 11 and the joint portion 12, and then pulls the slider 8 and the knob 9 simultaneously to pull the needle 2 together with the drill portion 6 out of the living tissue T and fully store them in the sheath 4 (FIG. 5E).

Next, in step S6, the operator removes the biopsy device 1 from the body by pulling the sheath 4 containing the drill portion 6 and the needle 2 out of the treatment instrument channel. This allows the living tissue T captured into the helical groove of the drill portion 6 and into the needle 2 to be collected as a specimen.

Thus, according to this embodiment, the rotating drill portion 6 is advanced by the rotation mechanism 10 at the lead equal to the pitch P1 of the drill portion 6. Consequently, the drill portion 6 can be properly inserted into the living tissue T while the drill portion 6 cuts the living tissue T into a helical shape. This allows the living tissue T to be efficiently taken into the helical groove and into the needle 2, and a sufficient amount of specimen can be accurately collected.

If the rotation is too slow relative to the advance of the drill portion 6, the drill portion 6 advances while pushing the living tissue T forward. This makes it difficult to efficiently capture the living tissue T into the helical groove and to cut the living tissue T into a helical shape by the drill portion 6.

If the rotation is too fast relative to the advance of the drill portion 6, the drill portion 6 advances while cutting the living tissue T into small pieces. This makes it difficult to cut the living tissue T into a continuous string and to capture the living tissue T into the needle 2.

When the drill portion 6 is pulled out of the living tissue T, the living tissue T that has entered the helical groove is caught by the drill portion 6, preventing the living tissue T once captured into the needle 2 from being pulled outward from the needle 2. This ensures that a sufficient amount of specimen can be collected.

In step S4, the needle 2 is inserted into the living tissue T at the same speed as the drill portion 6 while the wire 3 is positioned with respect to the needle 2 by the positioning mechanism 14. This allows the living tissue T that is cut out by the drill portion 6 and discharged to the proximal side to be efficiently collected in the needle 2.

The joint between the threaded portion 11 and the joint portion 12 can be released by the release mechanism 13. Therefore, when there is no need to rotate the drill portion 6 as in step S3, the wire 3 can be easily moved in the longitudinal direction with respect to the needle 2 without the need of rotation of the wire 3, by releasing the joint between the joint portion 12 and the threaded portion 11.

Since the drill portion 6 is exposed from the needle tip 2*a* after the living tissue T is captured into the needle 2, the same drill portion 6 can be used to collect specimens from other positions in the target living tissue T. For example, a fanning operation can be performed in such a manner that the needle tip 2*a* is positioned in multiple positions in the target living tissue T by movement of a curved portion of the ultrasound endoscope and specimens are collected from the multiple positions.

Second Embodiment

Next, a biopsy device and a specimen collection method according to the second embodiment of the present invention will be described with reference to the accompanying drawings.

In this embodiment, a configuration that differs from that in the first embodiment will be described, and description of the same configuration as in the first embodiment will be omitted using the same reference numerals.

FIGS. 8A to 8F illustrate operations of a biopsy device 100 used in the specimen collection method according to this embodiment. In this embodiment, a drill portion 6 is inserted into living tissue T, and then a needle 2 is inserted into the living tissue T along a wire 3. The biopsy device 100 of this embodiment differs from the biopsy device 1 of the first embodiment in an amount of protrusion d' of the drill portion 6 from a needle tip 2*a*.

Figure 6:
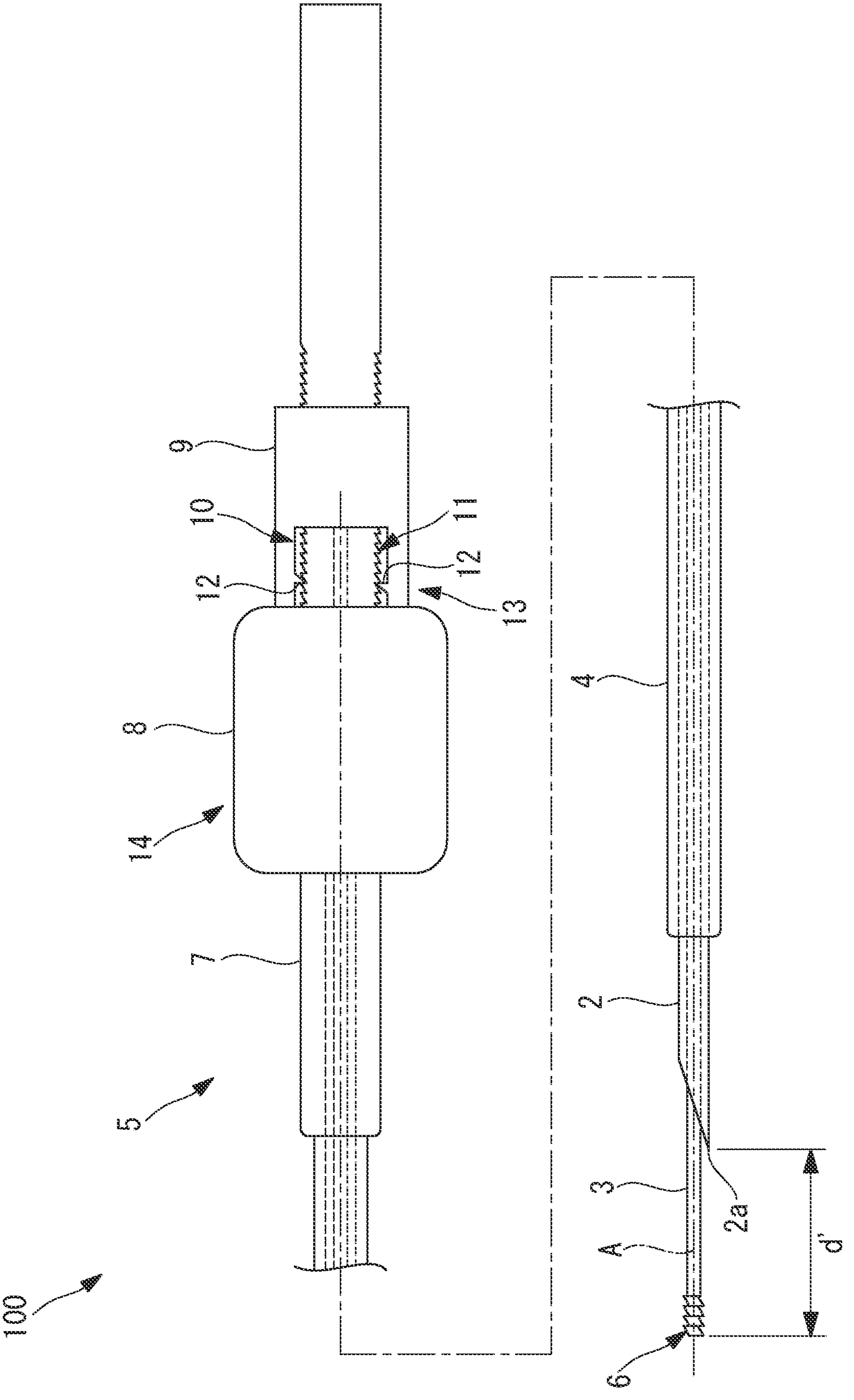
FIG. 6 is a diagram showing an overall configuration of a biopsy device according to a second embodiment, with a wire positioned by a positioning mechanism and a joint portion joined to a threaded portion.

As shown in FIG. 6, the biopsy device 100 according to this embodiment includes the needle 2, the wire 3, a sheath 4, an operating unit 5, a rotation mechanism 10, a release mechanism 13, and a positioning mechanism 14.

When a slider 8 and a knob 9 are located in the initial positions, the needle tip 2*a* and the drill portion 6 are accommodated in the sheath 4, as in the first embodiment.

In a state where the knob 9 butts against the slider 8, the entire drill portion 6 protrudes the predetermined distance d' from the needle tip 2*a*. The predetermined distance d' from the needle tip 2*a* to a distal end of the drill portion 6 is preferably greater than or equal to a thickness of the target living tissue T. For example, if the target living tissue T is a pancreatic tumor, since a size of the pancreatic tumor is often about 20 mm, the predetermined distance d' is preferably 20 mm or more.

The specimen collection method according to this embodiment will be described below.

Figure 7:
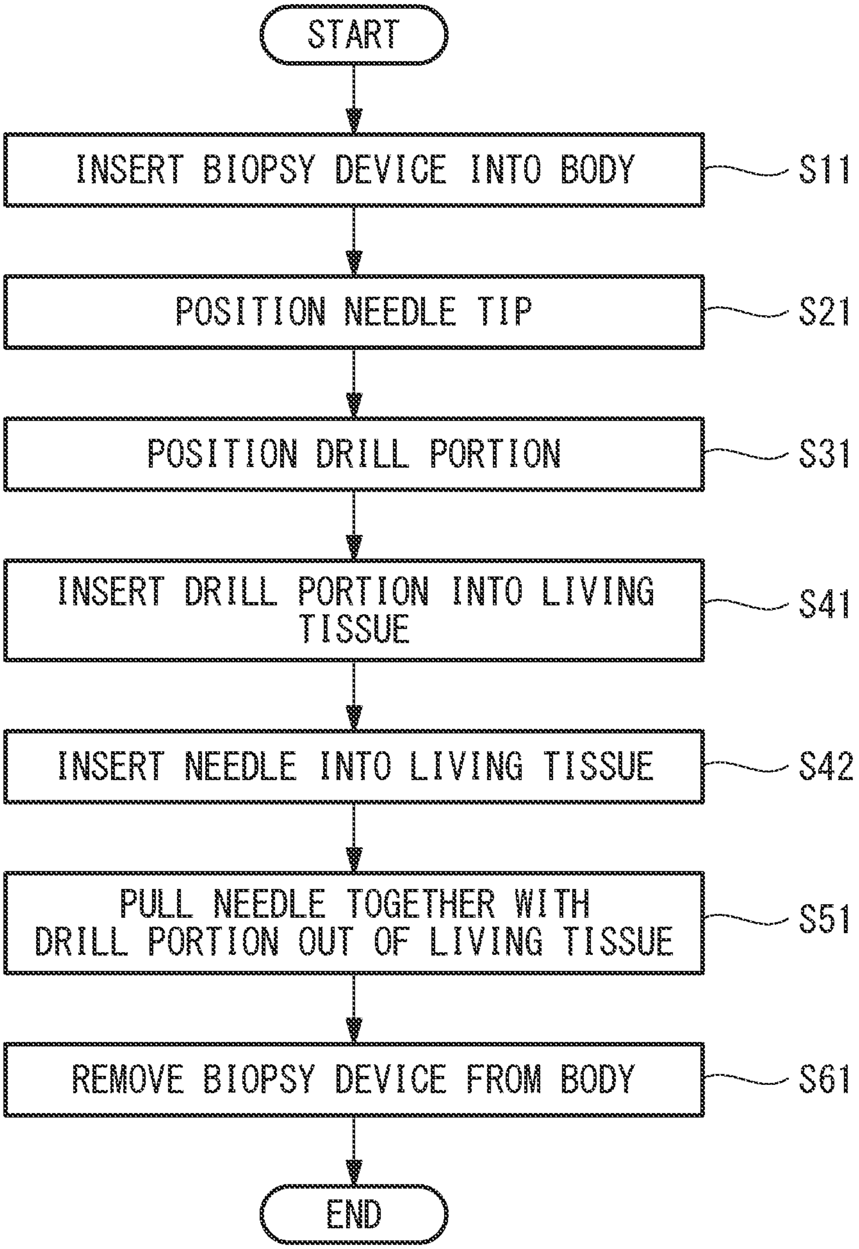
FIG. 7 is a flowchart of a specimen collection method according to the second embodiment.

As shown in FIG. 7, the specimen collection method includes step S11 of inserting the biopsy device 100 into the body, step S21 of positioning the needle tip 2*a* with respect to the target living tissue T, step S31 of positioning the drill portion 6 with respect to the living tissue T, step S41 of inserting the drill portion 6 into the living tissue T while rotating it, step S42 of inserting the needle 2 into the living tissue T along the wire 3, step S51 of pulling the needle 2 together with the drill portion 6 out of the living tissue T, and step S61 of removing the biopsy device 100 from the body.

Figure 8A:
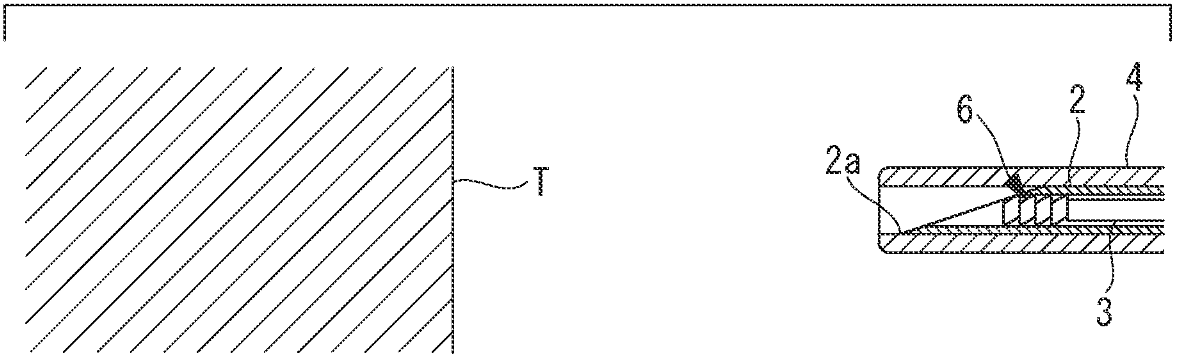
FIG. 8A is a diagram for explaining an operation of the biopsy device in step S11 of the specimen collection method.

As shown in FIG. 8A, an operator performs step S11 as in the first embodiment.

Figure 8B:
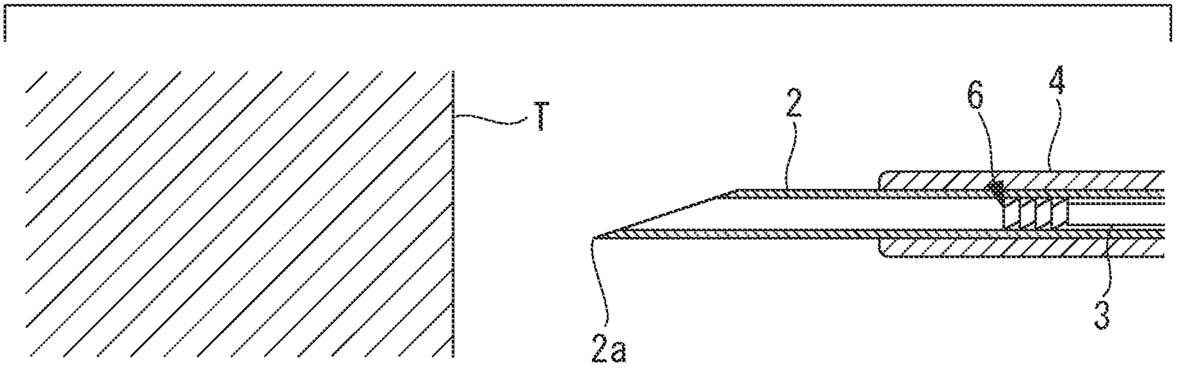
FIG. 8B is a diagram for explaining an operation of the biopsy device in step S21 of the specimen collection method.

Next, in step S21, in a state where the joint between a joint portion 12 and a threaded portion 11 is released, while observing an ultrasound image, the operator pushes the slider 8 to advance the needle 2, thereby positioning the needle tip 2*a* with respect to the target living tissue T (FIG. 8B).

Figure 8C:
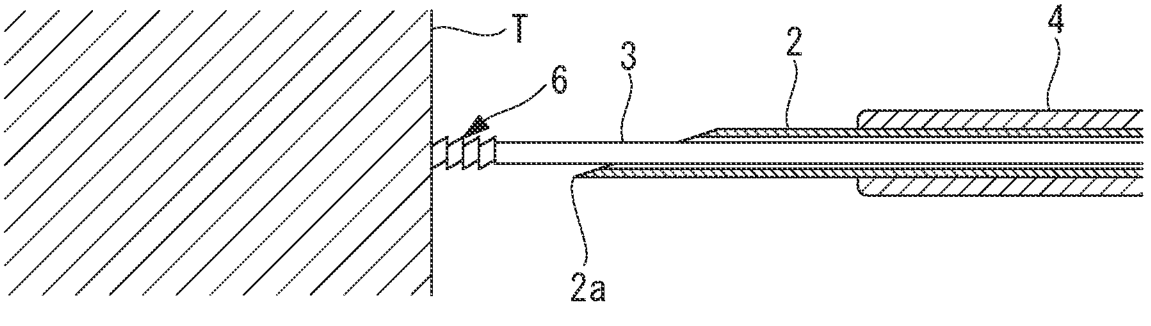
FIG. 8C is a diagram for explaining an operation of the biopsy device in step S31 of the specimen collection method.

Next, in step S31, the operator positions the drill portion 6 by pushing the knob 9 to advance the wire 3 to a position where the distal end of the drill portion 6 contacts the target living tissue T (FIG. 8C).

Figure 8D:
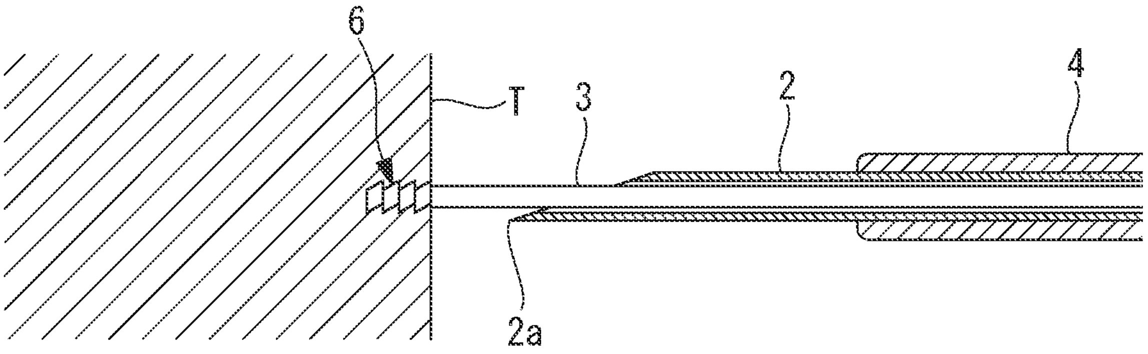
FIG. 8D is a diagram for explaining an operation of the biopsy device in step S41 of the specimen collection method.

Next, in step S41, the operator joins the joint portion 12 to the threaded portion 11 and then rotates the knob 9, thereby advancing the drill portion 6 and inserting it into the living tissue T (FIG. 8D). At this time, the drill portion 6 advances in a longitudinal direction with a lead equal to a predetermined pitch P1 while rotating about a longitudinal axis A with the rotation mechanism 10 consisting of the threaded portion 11 and the joint portion 12.

Figure 8E:
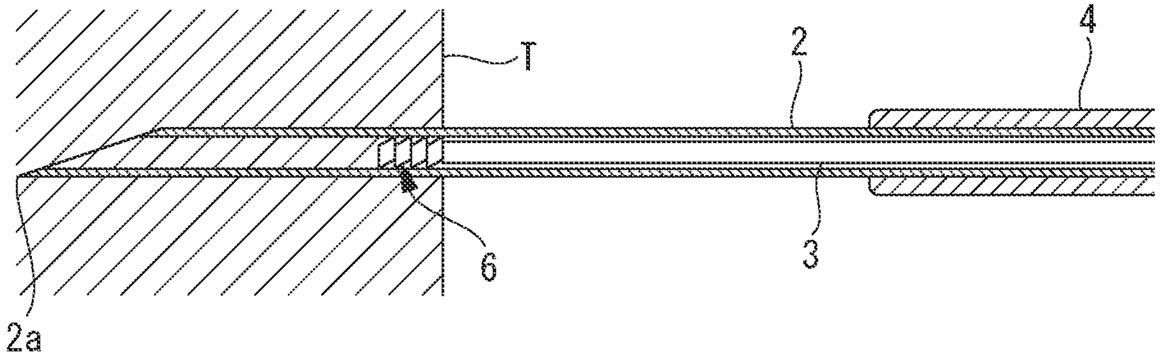
FIG. 8E is a diagram for explaining an operation of the biopsy device in step S42 of the specimen collection method.

Next, in step S42, the operator pushes the slider 8 to advance the needle 2, thereby inserting the needle 2 to a desired depth (a predetermined distance) in the living tissue T (FIG. 8E). This causes the living tissue T to be captured into the inside of the needle 2.

Figure 8F:
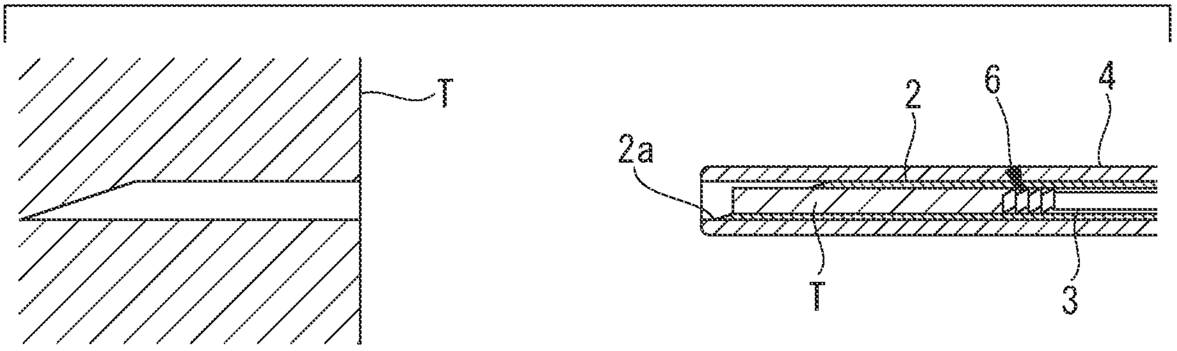
FIG. 8F is a diagram for explaining an operation of the biopsy device in step S51 of the specimen collection method.

Next, in step S51, the operator releases the joint between the threaded portion 11 and the joint portion 12, and then pulls the slider 8 and the knob 9 simultaneously to pull the needle 2 together with the drill portion 6 out of the living tissue T and fully store them in the sheath 4 (FIG. 8F).

Next, in step S61, the operator removes the biopsy device 100 from the body by pulling the sheath 4 containing the drill portion 6 and the needle 2 out of a treatment instrument channel. This allows the living tissue T captured into the needle 2 to be collected as a specimen.

Thus, according to this embodiment, when the drill portion 6 is inserted into the living tissue T, the rotating drill portion 6 advances with the lead equal to the pitch P1. Consequently, the drill portion 6 can be properly inserted into the living tissue T while the living tissue T is efficiently captured into the helical groove of the drill portion 6, and the drill portion 6 can be fixed to the living tissue T, serving as an anchor. Inserting the needle 2 into the living tissue T in this state prevents the living tissue T from being pushed and moved in an insertion direction by the needle 2, and allows a sufficient amount of the living tissue T to be accurately captured into the needle 2.

Since only the drill portion 6 is inserted into the living tissue T, a thicker column of the living tissue T can be captured into the needle 2 compared to the first embodiment, and more specimen suitable for diagnosis of the living tissue T can be collected.

When the needle 2 is pulled out of the living tissue T, the living tissue T is caught by the drill portion 6 in the needle 2, preventing the living tissue T once captured into the needle 2 from being pulled out of the needle 2. This makes it possible to collect a sufficient amount of specimen more accurately.

Figure 9A:
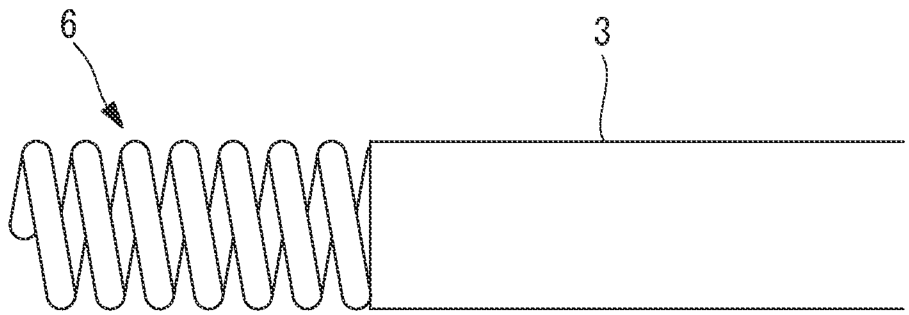
FIG. 9A is a diagram showing an example of a hollow drill portion.
Figure 9B:
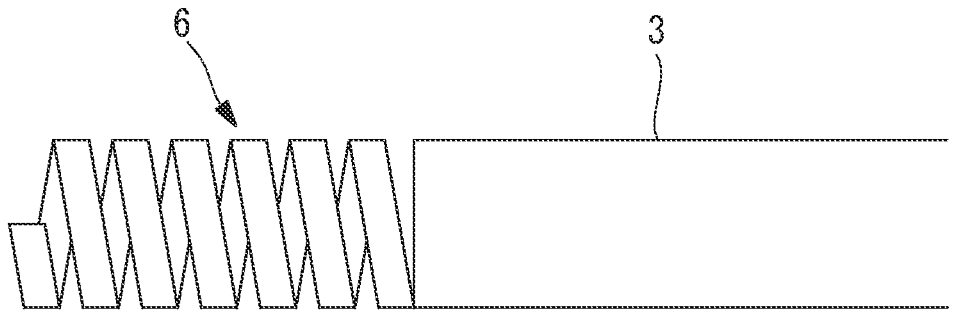
FIG. 9B is a diagram showing another example of the hollow drill portion.

Although the drill portion 6 is supposed to be solid in the first and the second embodiments described above, the drill portion 6 may be hollow instead as shown in FIGS. 9A and 9B.

In FIG. 9A, the drill portion 6 consists of spirally coiled fine wires. With this configuration, more specimen can be collected because the living tissue T is also captured into the inside of the drill portion 6 through gaps between the fine wires and an opening at a distal end surface.

In FIG. 9B, a cross section of the fine wire constituting the drill portion 6 is rectangular. With this configuration, the fine wire forms a flat surface that is substantially perpendicular to the insertion direction of the wire 3, so that when the drill portion 6 is pulled out of the living tissue T in steps S5 and S51, the living tissue T captured into the inside of the drill portion 6 is difficult to be pulled out, and a sufficient amount of specimen can be collected more accurately.

In the modification shown in FIGS. 9A and 9B, a thickness, an inner diameter, and a pitch P1 of the drill portion 6 are designed so that the drill portion 6 is rigid enough not to deform during insertion and withdrawal from the living tissue T.

Although the rotation mechanism 10 is provided in the operating unit 5 in the first and the second embodiments described above, the rotation mechanism 10 may be provided in another position.

If a distance from the rotation mechanism 10 to the drill portion 6 is long, the lead of the drill portion 6 may not exactly coincide with the pitch P2 of the rotation mechanism 10 (i.e., the pitch P1 of the drill portion 6) due to the transferability of rotation between the rotation mechanism 10 and the drill portion 6. To eliminate this inconvenience, the rotation mechanism 10 is preferably provided closer to the drill portion 6.

Figure 10:
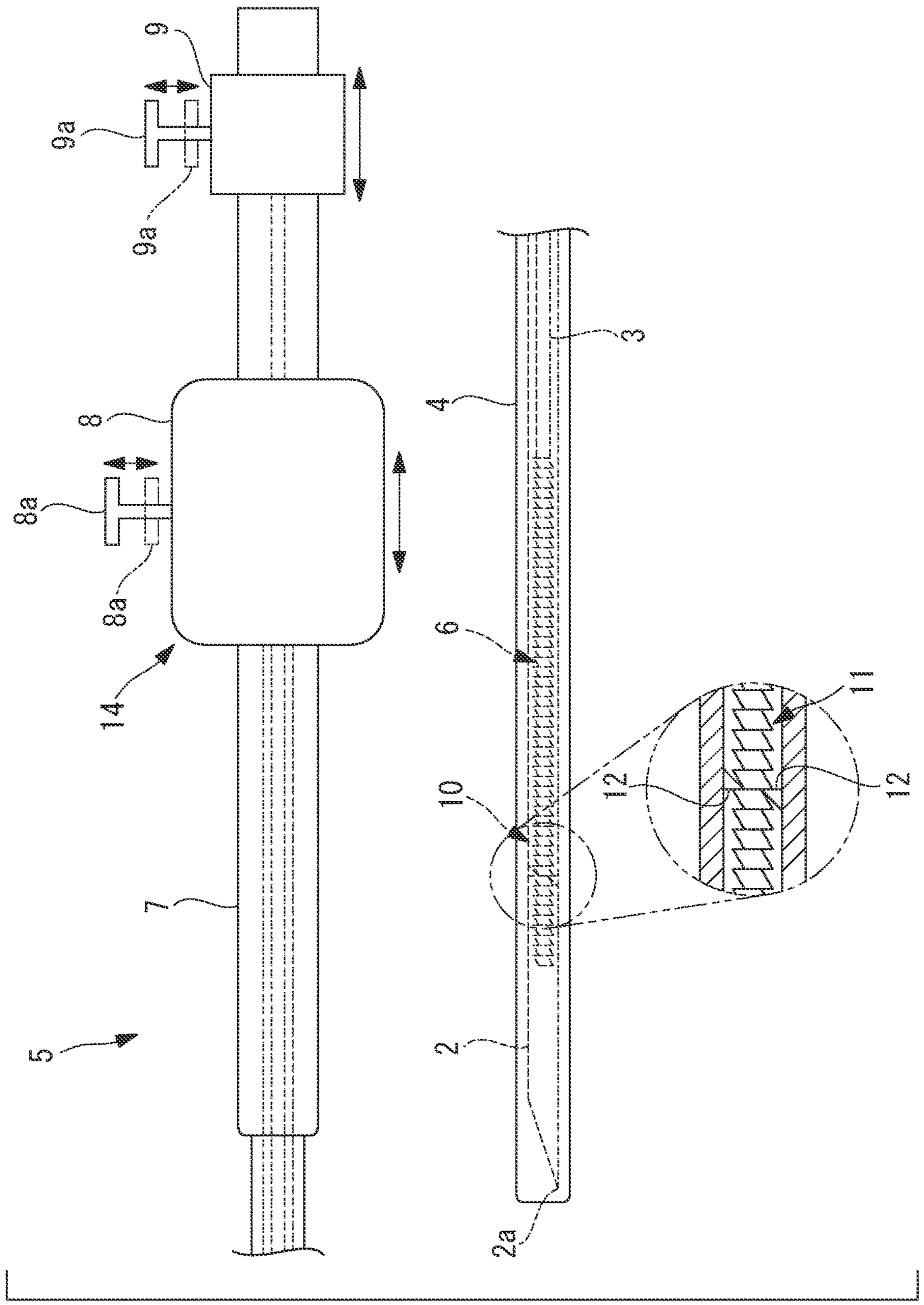
FIG. 10 is diagram showing an overall configuration of a modification of the biopsy device.

FIG. 10 shows an example in which the rotation mechanism 10 is provided on the needle 2 and the wire 3. In the biopsy device of FIG. 10, the rotation mechanism 10 includes the threaded portion 11 consisting of the drill portion (wire side member) 6 and the joint portion 12 provided on an inner circumference of the needle (peripheral member) 2 and configured to be joined to the helical groove of the drill portion 6. The slider 8 is provided with a locking unit 8*a* for fastening and unfastening the slider 8 to/from the main body 7, and the knob 9 is provided with a locking unit 9*a* for fastening and unfastening the knob 9 to/from the main body 7. In FIG. 10, the solid line locking units 8*a* and 9*a* indicate an unfastened state, and the double-dotted line locking units 8*a* and 9*a* indicate a fastened state.

As shown in FIGS. 11A to 11F, the biopsy device shown in FIG. 10 is used in the specimen collection method according to the second embodiment.

Figure 11A:
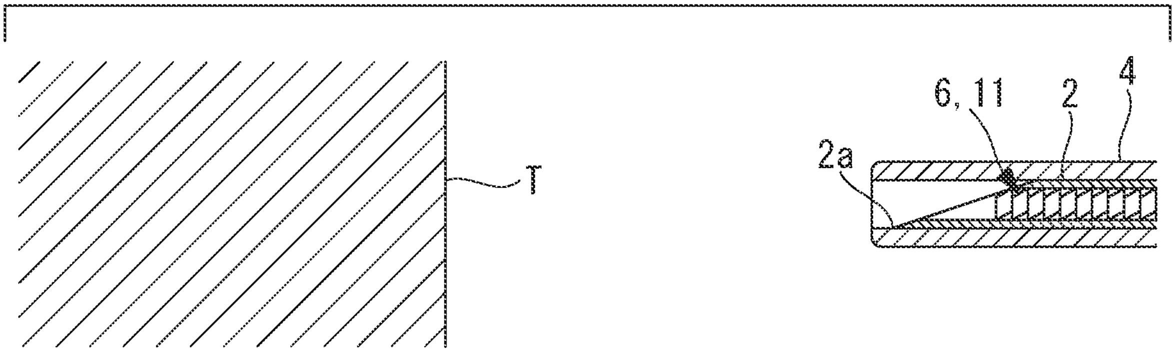
FIG. 11A is a diagram for explaining an operation of the biopsy device shown in FIG. 10 in step S11 of the specimen collection method.
Figure 11B:
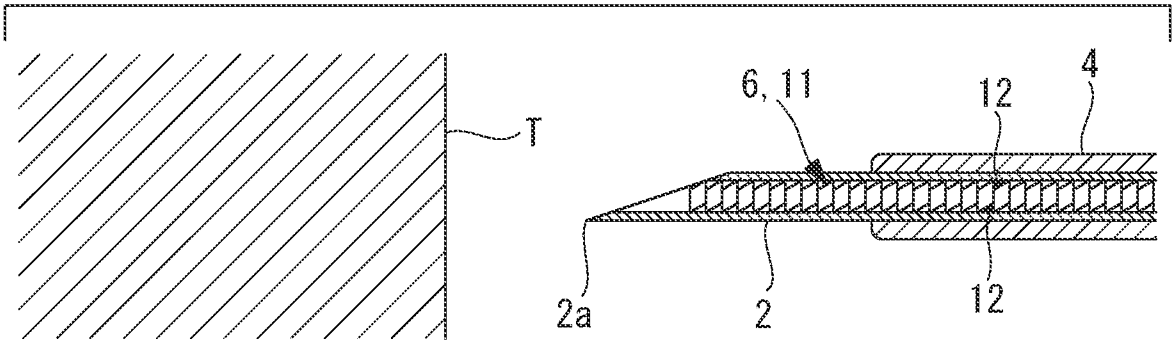
FIG. 11B is a diagram for explaining an operation of the biopsy device shown in FIG. 10 in step S21 of the specimen collection method.

After step S11 shown in FIG. 11A, as shown in FIG. 11B, with the locking units 8*a* and 9*a* unfastened, the slider 8 and the knob 9 are simultaneously pushed to advance the needle 2 and the wire 3 simultaneously (step S21).

Figure 11C:
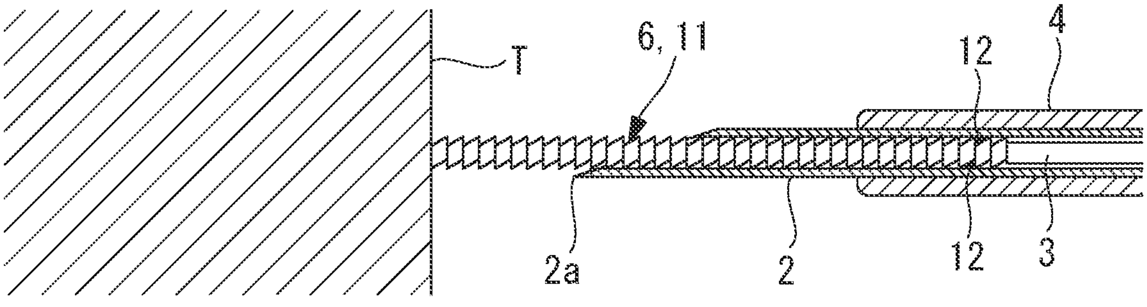
FIG. 11C is a diagram for explaining an operation of the biopsy device shown in FIG. 10 in step S31 of the specimen collection method.
Figure 11D:
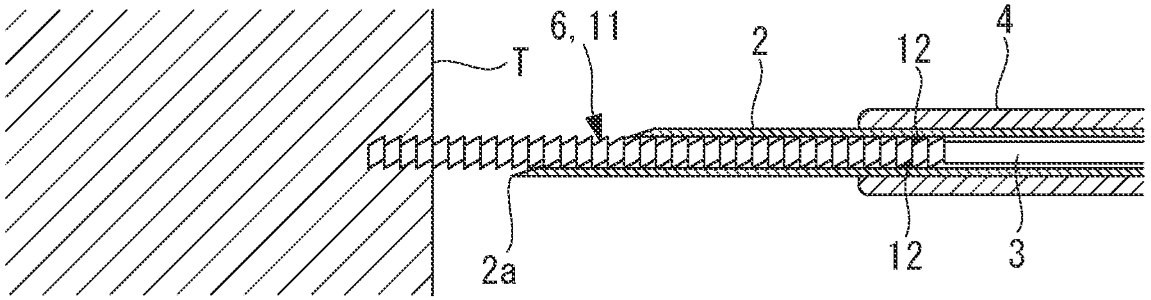
FIG. 11D is a diagram for explaining an operation of the biopsy device shown in FIG. 10 in step S41 of the specimen collection method.

Next, as shown in FIGS. 11C and 11D, the slider 8 is fastened through the locking unit 8*a* and the knob 9 is rotated to advance the drill portion 6 so that it is inserted into the living tissue T (steps S31 and S41).

Figure 11E:
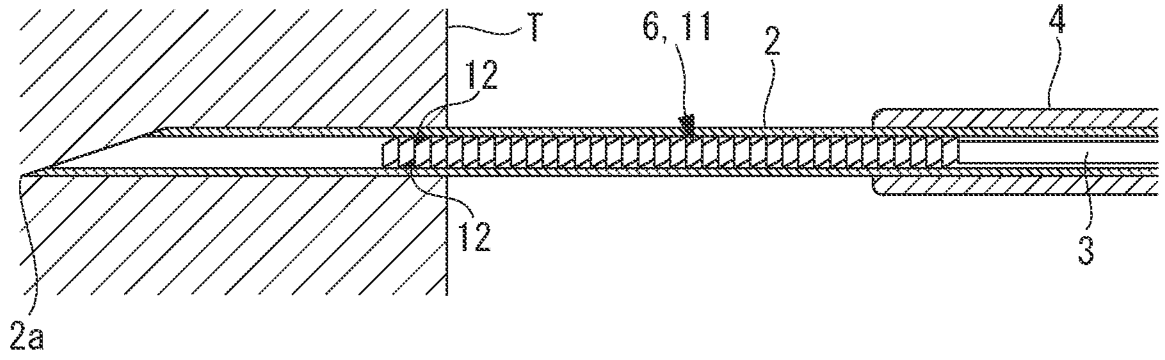
FIG. 11E is a diagram for explaining an operation of the biopsy device shown in FIG. 10 in step S42 of the specimen collection method.

Next, as shown in FIG. 11E, the knob 9 is fastened through the locking unit 9*a* and the slider 8 is unfastened through the locking unit 8*a*, and the slider 8 is rotated to advance the needle 2 so that the needle 2 is inserted to a desired depth into the target living tissue T (step S42).

Figure 11F:
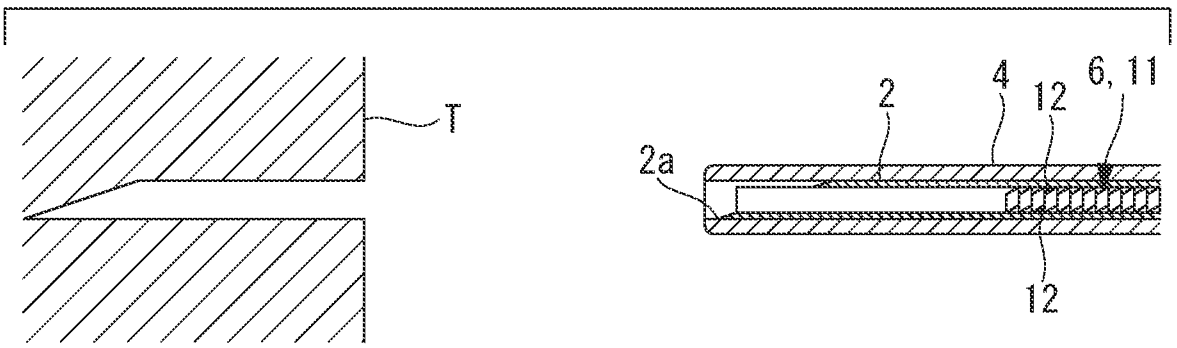
FIG. 11F is a diagram for explaining an operation of the biopsy device shown in FIG. 10 in step S51 of the specimen collection method.

Next, as shown in FIG. 11F, the knob 9 is unfastened through the locking unit 9*a* and the slider 8 and the knob 9 are pulled simultaneously, thereby pulling the needle 2 out of the living tissue T together with the drill portion 6 and completely storing them in the sheath 4 (step S51).

Figure 12:
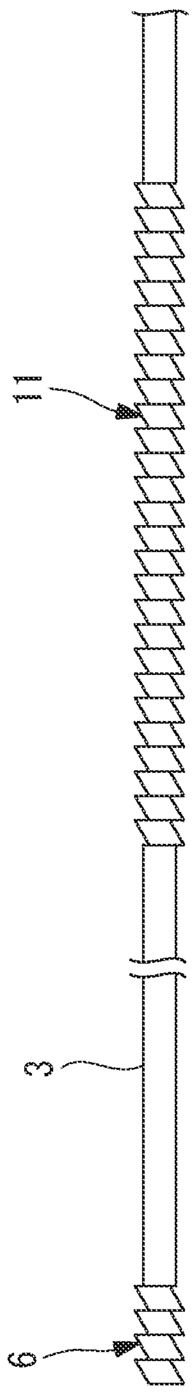
FIG. 12 is a diagram of a partial configuration of the wire for explaining a modification of the threaded portion.

Although the long drill portion 6 is used as the threaded portion 11 in FIG. 10, alternatively, as shown in FIG. 12, the threaded portion 11 different from the drill portion 6 may be provided on the wire 3. In this case, the threaded portion 11 can be provided in any position on the wire 3 that is proximal with respect to the drill portion 6. A position of the joint portion 12 is designed depending on a position of the threaded portion 11.

Figure 13:
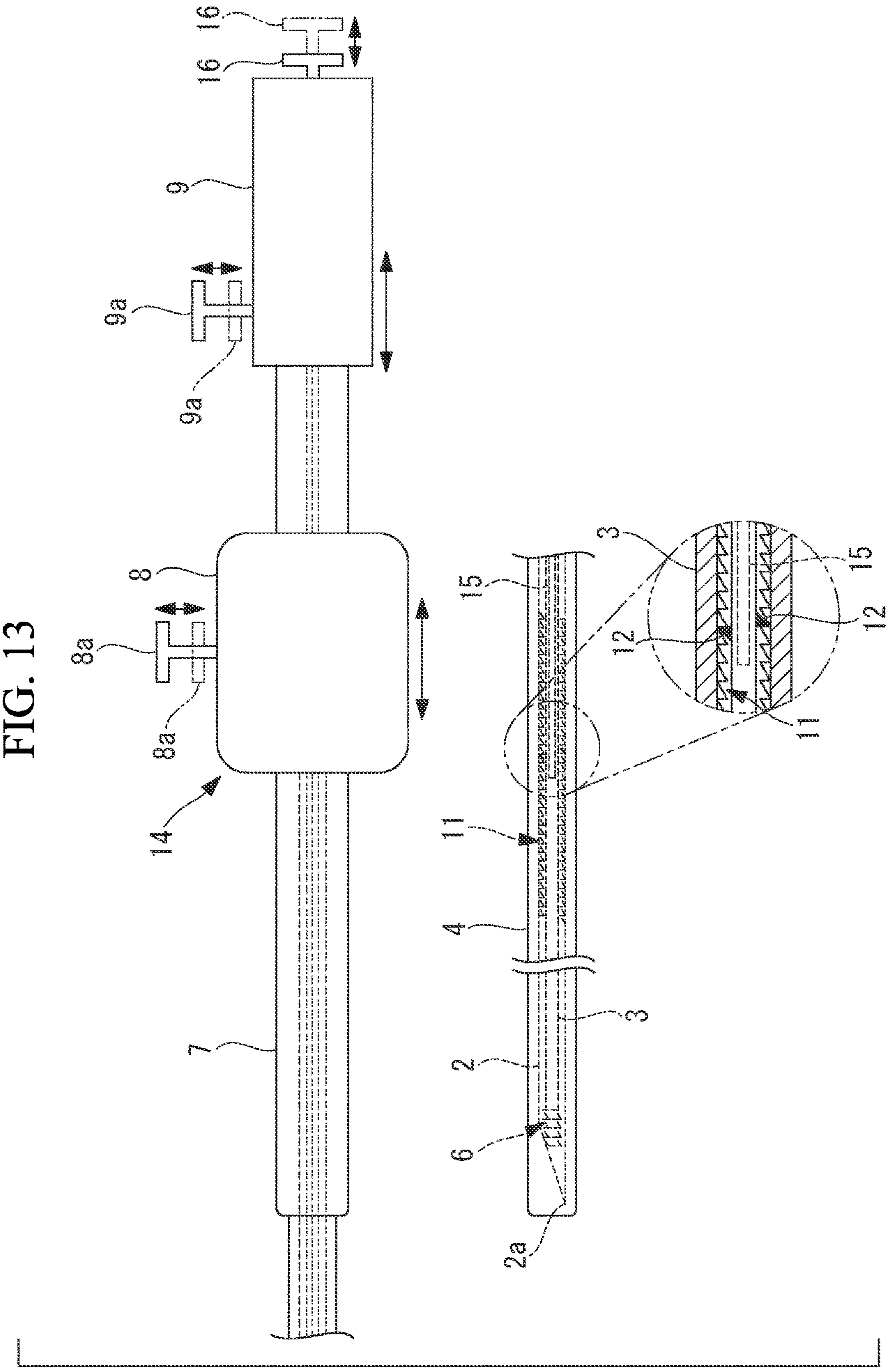
FIG. 13 is a diagram showing the overall configuration of another modification of the biopsy device.

In a configuration of the rotation mechanism 10 shown in FIG. 10, in order to move the needle 2 and the wire 3 relative to each other in the longitudinal direction either the needle 2 or the wire 3 needs to be rotated and the needle 2 and the wire 3 cannot be translationally moved relative to each other in the longitudinal direction. FIG. 13 shows a modification of the biopsy device including an additional release mechanism 13 to allow the wire 3 and the needle 2 to translationally move relative to each other.

The biopsy device shown in FIG. 13 includes a second wire 15 inserted into the wire 3 as a release mechanism 13. Thus, the wire 3 is at least partially hollow. The rotation mechanism 10 has the joint portion 12 on a first wire (wire side member) 3 and the threaded portion 11 on the needle (peripheral member) 2. The joint portion 12 is a projection protruding from an outer circumference of the first wire 3, and the projection may be a thread. The threaded portion 11 is a female threaded portion with a threaded groove provided on an inner circumference of the needle 2.

The knob 9 has a second knob 16 that is fixed to a distal end of the second wire 15 and configured to move the second wire 15 in the longitudinal direction. The operator can advance or retract the second wire 15 by pushing or pulling the second knob 16, thereby, as shown in FIGS. 14A and 14B, moving the joint portion 12 between a position where it is joined to the threaded portion 11 and a position where the joint to the threaded portion 11 is released.

Figure 14A:
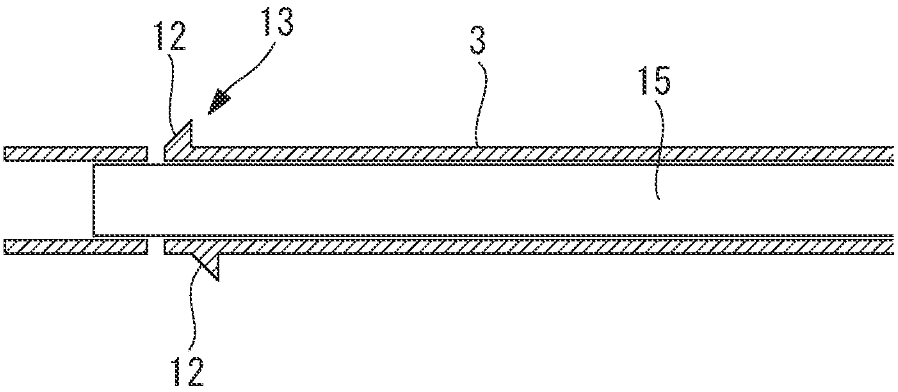
FIG. 14A is a diagram showing an operation of the joint portion brought with a second wire.
Figure 14B:
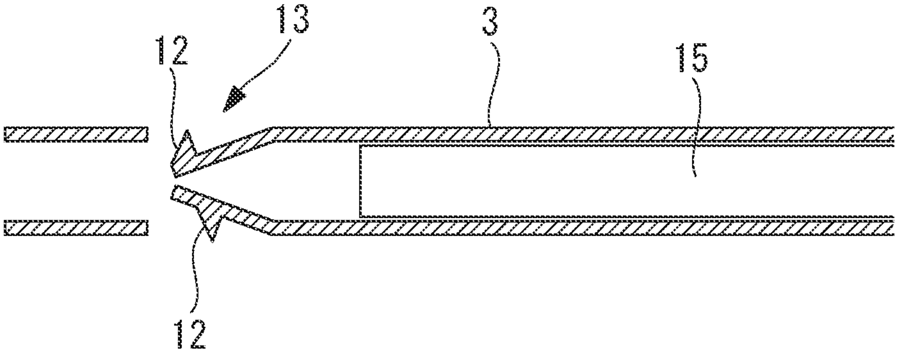
FIG. 14B is a diagram showing the operation of the joint portion brought with the second wire.

To be specific, as shown in FIG. 14B, a portion of a side wall of the first wire 3 where the joint portion 12 is provided is bent radially inward.

As shown in FIG. 14A, when the second wire 15 is inserted into the first wire 3 to a position beyond the joint portion 12, the joint portion 12 is pushed radially outward by the second wire 15 and is joined to the threaded portion 11.

As shown in FIG. 14B, when the second wire 15 is retracted until the distal end of the second wire 15 is located in a position that is proximal compared to the joint portion 12, a portion of the side wall of the first wire 3 bends radially inward and the joint portion 12 moves to an inward side of an outer diameter of the first wire 3, which releases the joint between the joint portion 12 and the threaded portion 11.

Although the embodiments of the present invention have been described in detail above with reference to the drawings, their specific configurations should not necessarily be limited to the above embodiments, and any design changes and the like can be made without departing from the gist of the present invention.

In particular, the phrases “equal in pitch” and “equal in lead” do not necessarily mean only completely “equal”, but also mean substantially equal without departing from the gist of the present invention, which is to ensure that a sufficient amount of specimen can be collected.

The components shown in the embodiments and the variations above can be used in appropriate combinations.

REFERENCE SIGNS LIST

1 Biopsy device
2 Needle
3 Wire
4 Sheath (peripheral member)
5 Operating unit
6 Drill portion
7 Main body (peripheral member)
8 Slider (positioning mechanism)
9 Knob (wire side member, release mechanism)
10 Rotation mechanism
11 Threaded portion (rotation mechanism)
12 Joint portion (rotation mechanism)
13 Release mechanism
14 Positioning mechanism
15 Wire (release mechanism)
16 Second knob
T Living tissue
A Longitudinal axis

The invention claimed is:

1. A biopsy device comprising:

a hollow needle;

a wire located inside the needle in a longitudinal direction of the needle and having a helical drill portion at a distal end portion;

a rotation mechanism configured to move the drill portion in the longitudinal direction, the drill portion protruding from a distal end of the needle and rotating about a longitudinal axis of the wire;

a long-length sheath covering the needle, the needle and the wire being movable in the longitudinal direction with respect to the sheath; and an operating unit provided on a proximal side of the needle, the wire, and the sheath, wherein the operating unit includes:

a main body fixed to a proximal end of the sheath;

a slider fixed to a proximal end of the needle and supported by the main body so as to be movable in the longitudinal direction; and a knob fixed to a proximal end of the wire, located proximally relative to the slider, and supported by the main body so as to be movable in the longitudinal direction and rotatable about the longitudinal axis, the rotation mechanism includes:

a threaded portion provided on the main body and having a pitch equal to a pitch of the drill portion; and a joint portion provided on the knob and being engaged with the threaded portion, and when the knob moves, with the joint portion engaged with the threaded portion, toward a distal side by being rotated, the slider moves toward the distal side together with the knob while abutting against the knob.

2. The biopsy device according to claim 1, wherein the wire and the needle are movable relative to each other in the longitudinal direction, the wire is positioned with respect to the needle to protrude a distal end of the drill portion a predetermined distance from the distal end of the needle when the slider abuts against the knob, and in a state where the slider abuts against the knob, the needle moves toward a distal side with movement of the wire toward the distal side.

3. The biopsy device according to claim 2, wherein the predetermined distance is 20 mm or more.

4. The biopsy device according to claim 1, wherein the joint portion is configured to move between being engaged with the threaded portion and being released from engagement with the threaded portion.

5. The biopsy device according to claim 1, wherein the drill portion is hollow.

6. The biopsy device according to claim 1, wherein the rotation mechanism is configured to move the drill portion in the longitudinal direction with a lead equal to the pitch.

7. The biopsy device according to claim 1, wherein when the knob is located in an initial position, the needle and the drill portion are accommodated in the sheath.

8. The biopsy device according to claim 1, wherein when the distal side of the knob abuts against the slider, a distal end of the drill portion protrudes a predetermined distance from the distal end of the needle.

9. The biopsy device according to claim 1, wherein a distal end of the knob abuts against a proximal end of the slider.

10. The biopsy device according to claim 1, wherein the knob moves toward the distal side to abut against the slider.

11. The biopsy device according to claim 1, wherein a distal end of the knob abuts against a proximal end of the slider so that a distal end of the drill portion protrudes a predetermined distance from the distal end of the needle.

12. The biopsy device according to claim 1, wherein the knob moves toward the distal side so that a distal end of the knob abuts against a proximal end of the slider.

13. The biopsy device according to claim 1, wherein the slider moves toward the distal side while abutting against the knob so that the drill portion is moved at a same longitudinal speed as the needle.

14. The biopsy device according to claim 1, wherein the slider moves toward the distal side while abutting against the knob so that the drill portion and the distal end of the needle move toward the distal side while a relative position between the slider and the knob is fixed.

* * * * *